US010651221B2

(12) United States Patent
Benahmed et al.

(10) Patent No.: US 10,651,221 B2
(45) Date of Patent: May 12, 2020

(54) IMAGE SENSOR FOR OBTAINING INFORMATION RELATING TO THE PHASE OF A LIGHT WAVE

(71) Applicant: Commissariat a l'energie atomique et aux energies alternatives, Paris (FR)

(72) Inventors: Selimen Benahmed, Grenoble (FR); Salim Boutami, Grenoble (FR); Olivier Cioni, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 16/222,061

(22) Filed: Dec. 17, 2018

(65) Prior Publication Data

US 2019/0189664 A1 Jun. 20, 2019

(30) Foreign Application Priority Data

Dec. 19, 2017 (FR) ..................................... 17 62492

(51) Int. Cl.
*H01L 27/14* (2006.01)
*H01L 31/00* (2006.01)
(Continued)

(52) U.S. Cl.
CPC ... *H01L 27/14629* (2013.01); *G01N 15/1456* (2013.01); *G01N 21/4788* (2013.01);
(Continued)

(58) Field of Classification Search
CPC ......... H01L 27/11582; H01L 27/14623; H01L 27/14685; H01L 27/14629; G01N 15/1456; G01N 21/4788; G01N 33/4833
(Continued)

(56) References Cited

U.S. PATENT DOCUMENTS

2011/0136165 A1 6/2011 Vojnovic et al.
2012/0012964 A1 1/2012 Kishi
(Continued)

FOREIGN PATENT DOCUMENTS

WO WO 2008/090330 A1 7/2008
WO WO 2010/113634 A1 10/2010

OTHER PUBLICATIONS

French Preliminary Search Report dated Oct. 10, 2018 in French Application 17 62492 filed on Dec. 19, 2017 (with English Translation of Categories of Cited Documents and Written Opinion).
(Continued)

*Primary Examiner* — David S Blum
(74) *Attorney, Agent, or Firm* — Oblon, McClelland, Maier & Neustadt, L.L.P.

(57) ABSTRACT

An object of the invention is an image sensor comprising a matrix of pixels, extending along a detection plane, and configured to form an image of an incident light wave propagating in a spectral band along a propagation axis, the image sensor being characterized in that it comprises a mask, formed by opaque elementary masks, extending parallel to the detection plane, between which there extend openings through which the incident light wave can propagate toward the detection plane, the matrix of pixels being divided into:
open pixels extending facing the openings;
masked pixels, each masked pixel being defined by a projection of an elementary mask along the axis of propagation on the matrix of pixels, each masked pixel being associated with the elementary mask facing it;
the image sensor comprising, between the open pixels and the openings:
a waveguide, extending facing masked pixels and open pixels;
(Continued)

a first diffraction grating, extending facing at least one open pixel, and configured to couple part of the incident light wave into the waveguide;

a second diffraction grating, extending facing a masked pixel, and configured to extract part of a guided wave propagating in the waveguide.

15 Claims, 8 Drawing Sheets

(51) Int. Cl.
    *H01L 31/0232*     (2014.01)
    *H01L 27/146*     (2006.01)
    *G01N 21/47*     (2006.01)
    *G01N 33/483*     (2006.01)
    *G01N 15/14*     (2006.01)
    *G01N 15/10*     (2006.01)

(52) U.S. Cl.
    CPC ... *G01N 33/4833* (2013.01); *H01L 27/14623* (2013.01); *H01L 27/14685* (2013.01); *G01N 2015/1006* (2013.01); *G01N 2015/1454* (2013.01)

(58) Field of Classification Search
    USPC .................................................. 257/431, 435
    See application file for complete search history.

(56) References Cited

U.S. PATENT DOCUMENTS

| | | |
|---|---|---|
| 2013/0083315 A1* | 4/2013 | Lo .............................. G01J 3/46 356/73 |
| 2016/0064436 A1 | 3/2016 | Uchida et al. |
| 2016/0153959 A1 | 6/2016 | Vojnovic et al. |
| 2017/0082975 A1* | 3/2017 | Gliere .................. G03H 1/0005 |

OTHER PUBLICATIONS

James R. Fienup, "Lensless coherent imaging by phase retrieval with an illumination pattern constraint", Optics Express, 2006, vol. 14, No. 2, pp. 498-508.

H.M. L. Faulkner, et al., "Movable Aperture Lensless Transmission Microscopy: A Novel Phase Retrieval Algorithm", Physical Review Letters, 2004, vol. 93, No. 2, The American Physical Society, pp. 023903-1-023903-4.

Manuel Guizar, et al., "Phase retrieval with transverse translation diversity: a nonlinear optimization approach", Optics Express, 2008, Vo. 16, No. 10, pp. 7264-7278.

J. C. H. Spence, et al., "Phase recovery and lensless imaging by iterative methods in optical, X-ray and electron diffraction", The Royal Society, 2002, 360, pp. 875-895.

Dirk Taillaert, et al., "Compact efficient broadband grating coupler for silicon-on-insulator waveguides", Optics Letters, vol. 29, No. 23, pp. 2749-2751.

* cited by examiner

IMAGE SENSOR FOR OBTAINING INFORMATION RELATING TO THE PHASE OF A LIGHT WAVE

TECHNICAL FIELD

The technical field of the invention is imaging, and more particularly phase imaging. The invention is particularly intended for the observation of translucent or transparent samples.

PRIOR ART

When transparent or low-opacity samples are to be observed, conventional imaging methods, based on the use of a lens focused on the sample, are usually unsuitable. Alternative methods have been developed, making it possible to form an image representing the phase difference between a light wave that has passed through the sample and a reference light wave that has not interacted with the sample. It is on this principle that phase imaging, or phase contrast, methods have been developed. These methods are based on the creation of interference between a light wave that has interacted with the sample and the reference light wave. This enables information about a phase difference to be converted into an intensity that can be measured by a standard image sensor.

However, such methods require precise set-ups, and are relatively difficult to use for low-cost routine testing. Moreover, they provide a relatively small field of observation.

WO2008090330 describes a device for observing translucent or transparent biological particles, in this case cells, by lensless imaging. By means of the device, an interference pattern can be associated with each cell, the morphology of the pattern allowing the type of cell to be identified. It is based on a simple image sensor, for example a matrix sensor of the CCD or CMOS type. Thus lensless imaging appears to be a simple and inexpensive alternative to phase microscopy. Moreover, it can provide a field of observation which is markedly more extensive than that of a microscope.

However, the image recorded by the image sensor includes no information about the phase. To obtain information representative of the phase, a holographic propagation operator must be applied to the image so as to reconstruct a phase image in which the phase contrasts due to the sample appear. Example of the application of holographic propagation operators are described in US2012/0218379, or alternatively in WO2017162985 or WO2016189257. These documents describe algorithms, usually iterative, which may be used for progressively obtaining information about the phase of a sample, while limiting the reconstruction noise. These algorithms are known as holographic reconstruction, or phase reconstruction, algorithms.

Such algorithms perform better when the image acquired by the image sensor has a high signal to noise ratio. To this end, EP3147646 describes a sample holder which is intended to be positioned facing an image sensor, and in which a one- or two-dimensional diffraction grating is arranged. The diffraction grating is designed to confine part of the incident light wave in a waveguide extending parallel to the image sensor. In a spectral band corresponding to a resonance spectral band of the diffraction grating, the image sensor is placed on a dark background. The waveguide is positioned in contact with the sample, in such a way that, when a particle of the sample is positioned near the waveguide, the light wave confined in the waveguide is locally decoupled, allowing the formation of a light beam that propagates as far as the image sensor. This device may be used to form diffraction patterns with a high signal to noise ratio. The image formed may subsequently be processed by a phase reconstruction algorithm.

The inventors wished to improve the performance of the existing lensless imaging devices, while limiting or even avoiding the use of phase reconstruction algorithms.

SUMMARY OF THE INVENTION

A first object of the invention is an image sensor comprising a matrix of pixels, extending along a detection plane, and configured to form an image of an incident light wave propagating, in a spectral band, along a propagation axis, the image sensor comprising a mask, formed by different opaque elementary masks, extending parallel to the detection plane, between which there extend openings through which the incident light wave can propagate toward the detection plane, the matrix of pixels being divided into:
  open pixels extending facing the openings;
  masked pixels, each masked pixel being defined by a projection of an elementary mask along the axis of propagation on the matrix of pixels, each masked pixel being associated with the elementary mask facing it;
the image sensor comprising, between the open pixels and the openings:
  a waveguide, forming a strip extending facing masked pixels and open pixels;
  a first diffraction grating, extending facing at least one open pixel, and configured to couple part of the incident light wave into the waveguide so as to form a guided wave, the first diffraction grating being configured to transmit another part of the incident light wave toward the open pixel, the first diffraction grating being associated with the open pixel;
  a second diffraction grating, extending facing a masked pixel, and configured to extract part of the guided wave propagating in the waveguide, so that the wave extracted in this way propagates toward the masked pixel, the second diffraction grating being associated with the masked pixel.

According to an embodiment:
  a masked pixel extends between two open pixels which are adjacent to it, each open pixel being associated with a first diffraction grating;
  the waveguide extends facing two open pixels and facing the masked pixel;
  the masked pixel is associated with a second diffraction grating, so as to extract light waves guided in the waveguide, resulting, respectively, from a coupling of the incident light wave by the first diffraction grating associated with each open pixel adjacent to the masked pixel.

The masked pixel and the open pixels adjacent to it might be arranged along a same row or along a same column of the matrix of pixels.

According to one embodiment:
  a masked pixel extends between two open pixels, which are adjacent to it, along a row of the matrix of pixels, each open pixel being associated with a first diffraction grating;
  the waveguide extends facing the two open pixels and facing the masked pixel, parallel to the row, forming a longitudinal waveguide, each first diffraction grating associated with the open pixels of the row being configured to couple part of the incident light wave into the longitudinal waveguide;

the masked pixel is associated with a second diffraction grating, so as to extract light waves guided in the longitudinal waveguide, in such a way that the light waves extracted in this way are detected by the masked pixel;

the masked pixel extends between two open pixels, which are adjacent to it, along a column of the matrix of pixels, said open pixels of the column being associated with a first diffraction grating;

the sensor comprises a lateral waveguide extending parallel to the column, facing the two open pixels of the column and facing the masked pixel, each first diffraction grating associated with the open pixels of the column being configured to couple part of the incident light wave into the lateral waveguide;

the second diffraction grating is configured to extract light waves propagating in the lateral waveguide, in such a way that the light waves extracted in this way are detected by the masked pixel.

According to one embodiment, the first diffraction grating is formed by a first thin layer, extending parallel to the waveguide, the first thin layer being formed from a first material, the first thin layer comprising inclusions of a first auxiliary material, the respective refractive indices of the first material and of the first auxiliary material being different, the first material and the first auxiliary material being transparent in part or all of the spectral band;

the second diffraction grating is formed by a second thin layer, extending parallel to the waveguide, the second thin layer being formed from a second material, the second thin layer comprising inclusions of a second auxiliary material, the respective refractive indices of the second material and of the second auxiliary material being different.

The first diffraction grating and/or the second diffraction grating may be one- or two-dimensional.

Each first diffraction grating may form an injection grating, for injecting part of the incident light wave into a waveguide extending along an axis. In this case, each first diffraction grating may be one-dimensional.

Each first diffraction grating may form an injection grating, for injecting part of the incident light wave into two waveguides extending, respectively, along different axes, notably orthogonal axes. In this case, each first diffraction grating may be two-dimensional.

Each second diffraction grating may form an extraction grating, for extracting part of a light wave propagating in a waveguide extending along an axis. In this case, each second diffraction grating may be one-dimensional.

Each second diffraction grating may form an extraction grating, for extracting part of a light wave propagating in waveguides extending, respectively, along different axes, notably orthogonal axes. In this case, each second diffraction grating may be two-dimensional.

According to one embodiment, the first material and the second material form the same material. It is preferably transparent to the spectral band of the incident light wave.

Preferably, the second auxiliary material is a metal.

According to one embodiment, the first diffraction grating and the second diffraction grating extend along the same plane, preferably orthogonal or substantially orthogonal to the propagation axis.

According to one embodiment, the first diffraction grating and the second diffraction grating extend parallel to the matrix of pixels.

According to one embodiment, at least one elementary mask comprises a reflective face, facing a masked pixel associated with the elementary mask, so as to reflect part of the light wave extracted from the second waveguide, extending facing the masked pixel, toward the latter.

A second object of the invention is a device for observing a sample, comprising:
 a light source configured to emit an illuminating light wave in a spectral band, the illuminating light wave propagating along a propagation axis, toward the sample;
 an image sensor;
 a holder configured to receive the sample, so that the sample extends between the light source and the sample, the image sensor being configured to detect an incident light wave propagating between the sample and the sensor when the sample is illuminated by the illuminating light wave;

the image sensor being a sensor according to the first object of the invention.

A third subject of the invention is a method for determining an intensity and a phase of a light wave, using an image sensor according to the first object of the invention, the image sensor being such that:
 a masked pixel extends along a row or a column between two open pixels;
 the waveguide extends facing the open pixels and facing the masked pixel, along the row or along the column;
 each of the open pixels is associated with a first diffraction grating;
 the masked pixel is associated with a second diffraction grating;

the method comprising:
 a) illuminating the sensor in such a way that an incident light wave propagates toward each open pixel;
 b) coupling part of the incident light wave, by means of the first diffraction grating extending facing each open pixel, in such a way that:
  at the first diffraction grating, a confined light wave propagating in the waveguide is formed;
  a transmitted light wave is transmitted to the open pixel associated with the first diffraction grating;
 c) extracting, by means of the second diffraction grating, part of each confined light wave propagating in the waveguide, so as to form an extracted light wave;
 d) detecting the extracted light wave by the masked pixel;
 e) obtaining, on the basis of an intensity of the extracted light wave, information relating to the phase difference of the incident light wave propagating toward each open pixel, respectively;
 f) detecting the light wave transmitted by the first diffraction grating toward each open pixel associated with the first diffraction grating, in order to obtain an intensity of the transmitted light wave representative of the intensity of the light wave incident on the open pixel.

According to one embodiment, the method comprises:
 g) estimating a phase of the light wave detected by each open pixel on the basis of the phase difference obtained in e).

According to one embodiment, the open pixels are positioned along the same row or the same column of the matrix of pixels; g) comprises taking into account a reference phase value, obtained on a pixel of the row or of the column.

According to one embodiment, the sensor comprises different masked pixels, each masked pixel being positioned between at least two open pixels along the same row and two open pixels along the same column; a) to f) are carried out on each masked pixel as well as on the open pixels between which the masked pixel is positioned, and g) is carried out on the basis of a phase difference determined on the basis of an intensity of a light wave detected by each masked pixel.

Other advantages and characteristics will be more clearly apparent from the following description of specific embodiments of the invention, provided by way of non-limiting example and represented in the figures listed below.

FIGURES

Figure 4A:
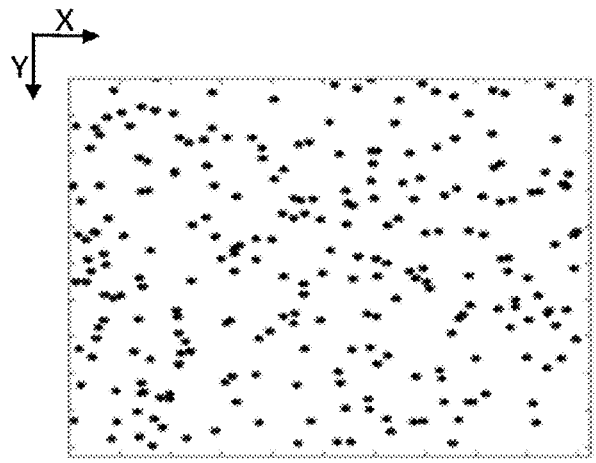
FIGS. 4A and 4B show images of the absorption and phase of a surface sample modeled for the purpose of simulations.
Figure 4B:
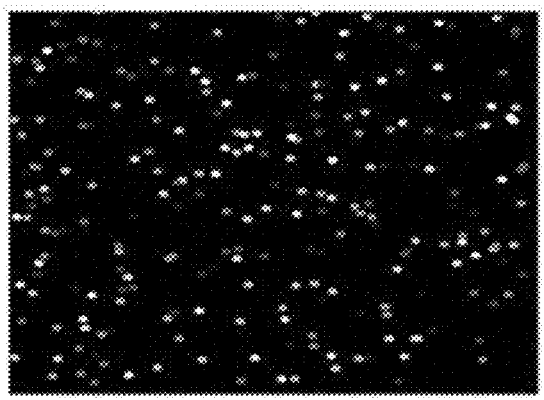
Figure 4C:
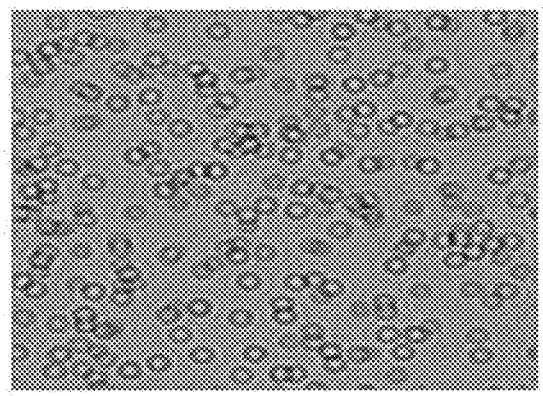
FIGS. 4C and 4D show, respectively, images of the module and phase of a light wave that has passed through the sample shown in FIGS. 4A and 4B and reaches the detection plane defined by the image sensor.
Figure 4D:
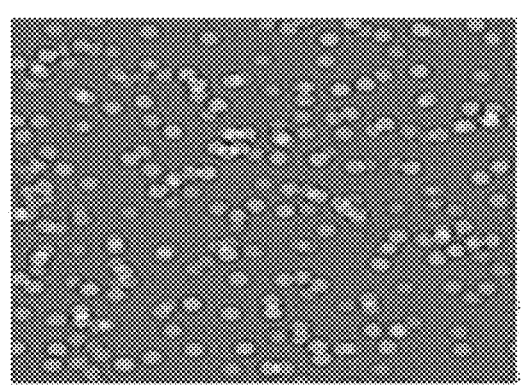
Figure 4E:
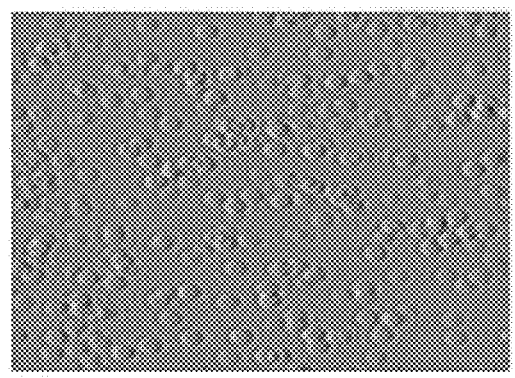
FIG. 4E is obtained from FIG. 4D. It shows the phase differences between two adjacent pixels of the same line.
Figure 4F:
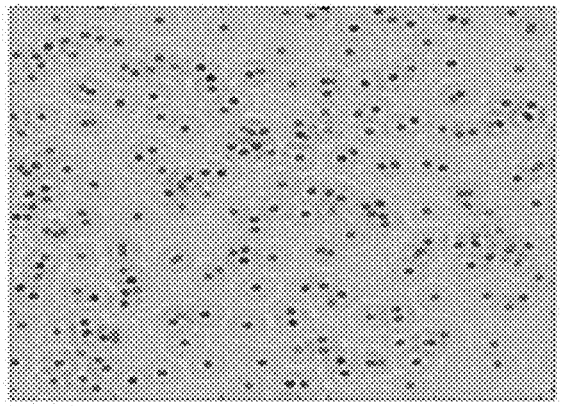
FIGS. 4F and 4G are results of reconstructions of the modulus and the phase, respectively, of the light wave, based on the image of FIG. 4C.
Figure 4G:
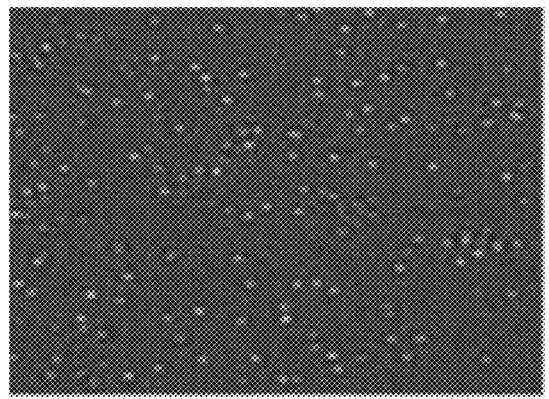
Figure 4H:
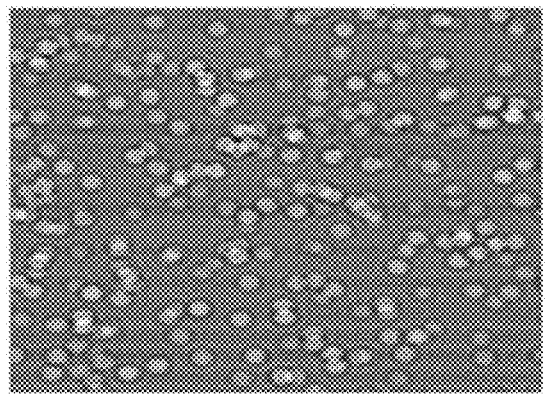

FIG. 4H corresponds to an image of the phase of the light wave incident on the sensor, in the detection plane. This image is obtained on the basis of the phase differences shown in FIG. 4E, using, on each line, phase values called reference values, obtained in FIG. 4G.

Figure 4I:
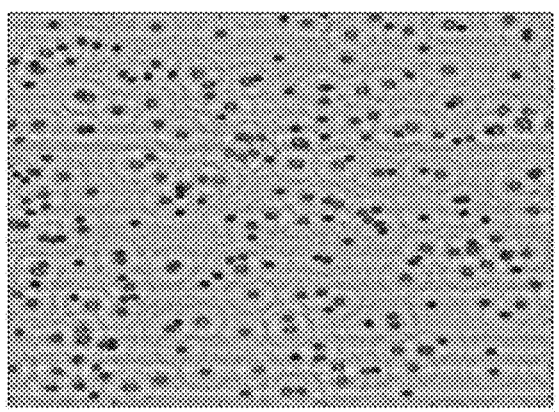
Figure 4J:
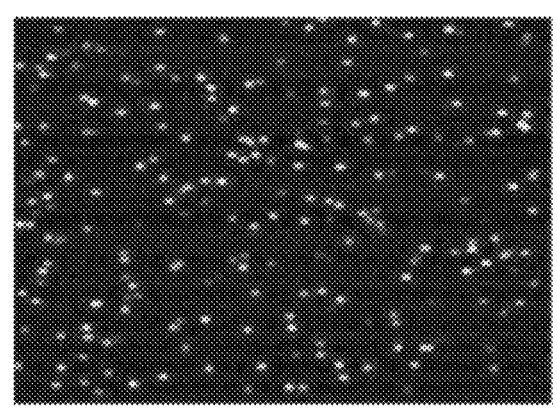

FIGS. 4I and 4J are images of the modulus and the phase of the light wave incident on the sensor, in the plane of the sample. These images are obtained by holographic reconstruction based on images 4F and 4G.

DESCRIPTION OF PARTICULAR EMBODIMENTS

Figure 1A:
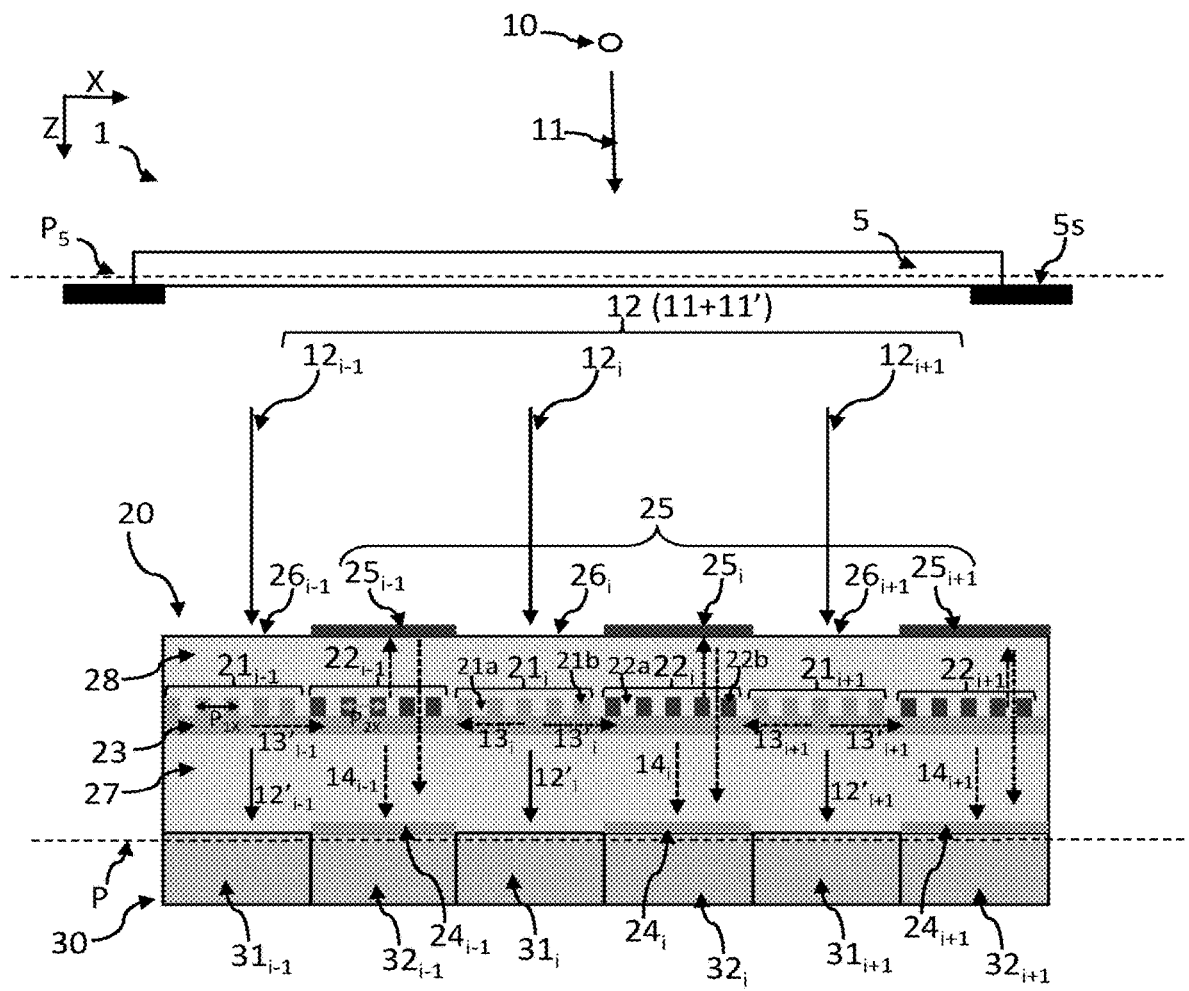
FIG. 1A shows a device for observing a sample according to the invention.

FIG. 1A shows a device for observing a sample according to the invention. The device 1 comprises a light source 10, configured to illuminate a sample 5. The light source 10 is configured to emit an illuminating light wave 11 propagating toward the sample along a propagation axis Z, in a spectral band $\Delta\lambda$.

The sample 5 is a transparent or translucent sample that is to be characterized. It may, for example, be a liquid, comprising particles. The liquid may comprise a biological fluid, for example blood or a blood extract, or any other liquid, for example lymph, urine, cerebrospinal fluid, etc. The liquid may also be a cell culture medium, or a liquid collected from the environment or from an industrial installation. The particles may be cells or microorganisms, for example bacteria, yeasts or spores. They may also be microbeads, lipid particles, or solid particles. The sample may also be solid, or may be in the form of a gel. It may, for example, be a thin tissue slide that is to be characterized, for example a pathological anatomy slide. The sample is positioned on a sample holder 5s. The sample holder defines a sample plane $P_S$, such that, when the sample is positioned on the holder, it extends along the sample plane $P_S$. The sample plane $P_S$ is preferably orthogonal, or substantially orthogonal, to the propagation axis Z of the illuminating light wave 11. "Substantially orthogonal" is taken to mean that the plane forms an angle of 90° subject to an angular tolerance of ±10° or ±20°, for example. The sample may be positioned in a fluid chamber, or any other transparent container, or on a transparent slide. The thickness of the sample, according to the propagation axis Z, is preferably less than 1 cm, and is usually less than 5 mm or 1 mm.

The light source 10 may be a laser light source or a light-emitting diode light source. It may be coupled to a band pass filter, not shown in FIG. 1A, so as to limit the spectral band $\Delta\lambda$ of the light wave 11 reaching the sample 5. As described below, the device 1 comprises an image sensor 20, comprising diffraction gratings whose characteristics are adapted to a resonance wavelength $\lambda$. The spectral band $\Delta\lambda$ must therefore extend around the resonance 30 wavelength $\lambda$ described below. The width of the spectral band $\Delta\lambda$ of the illuminating light wave 11 is preferably less than 100 nm, or possibly less than 50 nm or 10 nm, so that the light wave 11 may resemble a monochrome wave. "Bandwidth" is taken to mean a width at mid-height in the spectral band. Preferably, light source is a point source, such that the light wave reaches the sample 5 in the form of a plane wave, propagating along the propagation axis Z. The light source 10 may be associated with a diaphragm. If the light source comprises a diaphragm, a diffuser is preferably inserted between the light source and the diaphragm, as described in US2017317125. The light source 10 may also be formed by an end of an optical fiber, another end of which is coupled to a light source. In particular, it may be a single-mode optical fiber.

Part of the illuminating light wave 11 is transmitted by the sample 5, with no interaction, or only negligible interaction, with the latter. Another part of the light wave 11 interacts with the sample, and is, for example, diffracted by the latter.

The device comprises an image sensor 20. In the example shown in FIG. 1A, the sample 5 is positioned between the light source 10 and the image sensor 20. The image sensor 20 receives a light wave 12, called the incident light wave, comprising:
  part of the illuminating light wave 11 transmitted by the sample;
  a diffracted light wave 11', resulting from the diffraction by the sample of the illuminating light wave 11.

The incident light wave 12, to which the image sensor 20 is exposed, propagates along the propagation axis Z toward the image sensor.

In the example shown in FIG. 1A, no optical image forming system is positioned between the sample 5 and the image sensor 20. Thus the image sensor is configured in what is called a lensless imaging configuration.

In the prior art methods, the incident light wave 12 is detected with the aid of a standard image sensor. Subsequently, holographic reconstruction algorithms are used to determine a phase of the light wave 12, particularly in the plane of the sample $P_S$. The image sensor 20 described below limits the use of such reconstruction algorithms. It is distinguished from the prior art in that it allows access to phase information about the incident light wave 12, as described below.

Conventionally, the image sensor 20 comprises a matrix of pixels 30 extending along a plane P forming a detection plane. The pixels are formed in a silicon substrate, by CMOS technology. The detection plane P is preferably orthogonal, or substantially orthogonal, to the propagation axis Z.

The image sensor comprises a mask 25, positioned upstream of the matrix of pixels 30. The term "upstream" is to be understood according to the direction of propagation of the light. The mask 25 comprises elementary masks $25_i$ which are opaque in the spectral band $\Delta\lambda$. Each elementary mask $25_i$ preferably extends parallel to the matrix of pixels 30. The index i is an integer corresponding to a position of the elementary mask perpendicular to the axis Z. Taking into account the direction of propagation Z, each elementary mask $25_i$ is projected on the matrix of pixels 30, so as to form what are called masked pixels $32_i$ on the matrix. In the example shown, the size of an elementary mask $25_i$ corresponds to the size of one pixel, the latter measuring 1 µm×1 µm. More generally, the size of each pixel is preferably less than 10 µm×10 µm.

Thus, each elementary mask $25_i$ is associated with a masked pixel $32_i$, the masked pixel extending to face the elementary mask $25_i$ with which it is associated, along the axis of propagation Z. In this example, each elementary mask $25_i$ is formed by an aluminum layer with a thickness of 100 nm along the axis Z. An elementary mask $25_i$ may be made by using another material, provided that the material is opaque in the spectral band $\Delta\lambda$. FIG. 1A shows three elementary masks $25_{i-1}$, $25_i$, and $25_{i+1}$.

Openings 26 extend between two adjacent elementary masks $25_{i-1}$, $25_i$. Each opening is transparent in the spectral band $\Delta\lambda$. FIG. 1A shows an opening $26_i$ extending between two adjacent elementary masks $25_{i-1}$ and $25_i$, as do two other openings $26_{i-1}$ and $26_{i+1}$. The dimension of an opening, parallel to the detection plane P, preferably corresponds to the dimension of at least one pixel of the matrix of pixels 30. Thus, in a similar way to the elementary masks $25_i$, each opening $26_i$ is projected, along the propagation axis Z, on the matrix of pixels 30, forming a pixel $31_i$ called an open pixel. Thus each open pixel $31_i$ is associated with an opening $26_i$, the latter being located facing the open pixel $31_i$ along the propagation axis Z. Each open pixel $31_i$ is associated with an opening $26_i$, positioned facing the latter along the propagation axis Z. An opening $26_i$ may be formed from a transparent material or a space left free, adjacent to an elementary mask $25_i$. FIG. 1A shows light waves $12_{i-1}$, $12_i$ and $12_{i+1}$ propagating, respectively, through the openings $26_{i-1}$, $26_i$ and $26_{i+1}$ toward the open pixels $31_{i-1}$, $31_i$ and $31_{i+1}$. The light waves $12_{i-1}$, $12_i$ and $12_{i+1}$ form the incident light wave 12 to which the image sensor 20 is exposed.

In the examples described below, the mask is arranged to form a checkerboard extending parallel to the detection plane P. The pixels of the matrix of pixels are arranged in rows and columns. Each row and each column comprises open pixels $31_{i-1}$, $31_i$ and $31_{i+1}$ and masked pixels $32_{i-1}$, $32_i$ and $32_{i+1}$ positioned alternately.

Figure 1B:
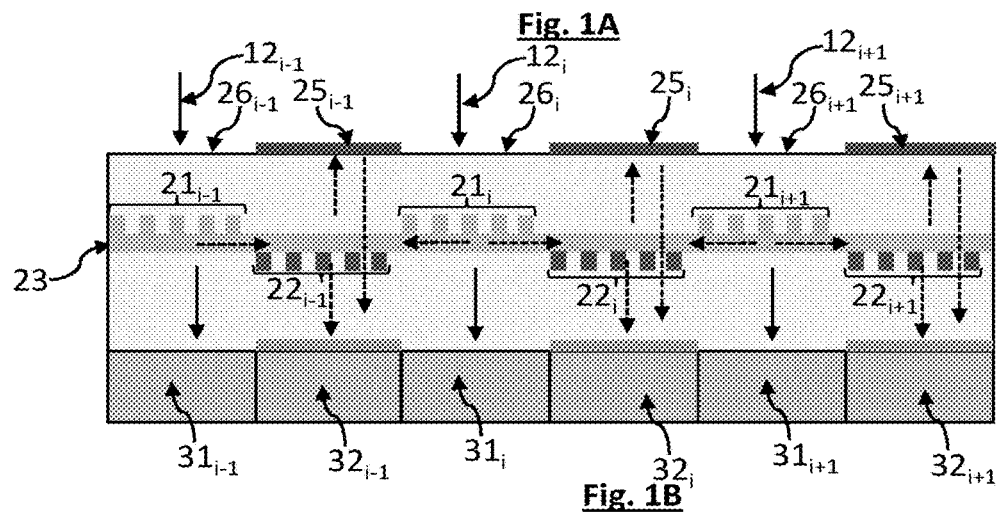
FIG. 1B shows a variant of a sensor according to the invention.
Figure 1C:
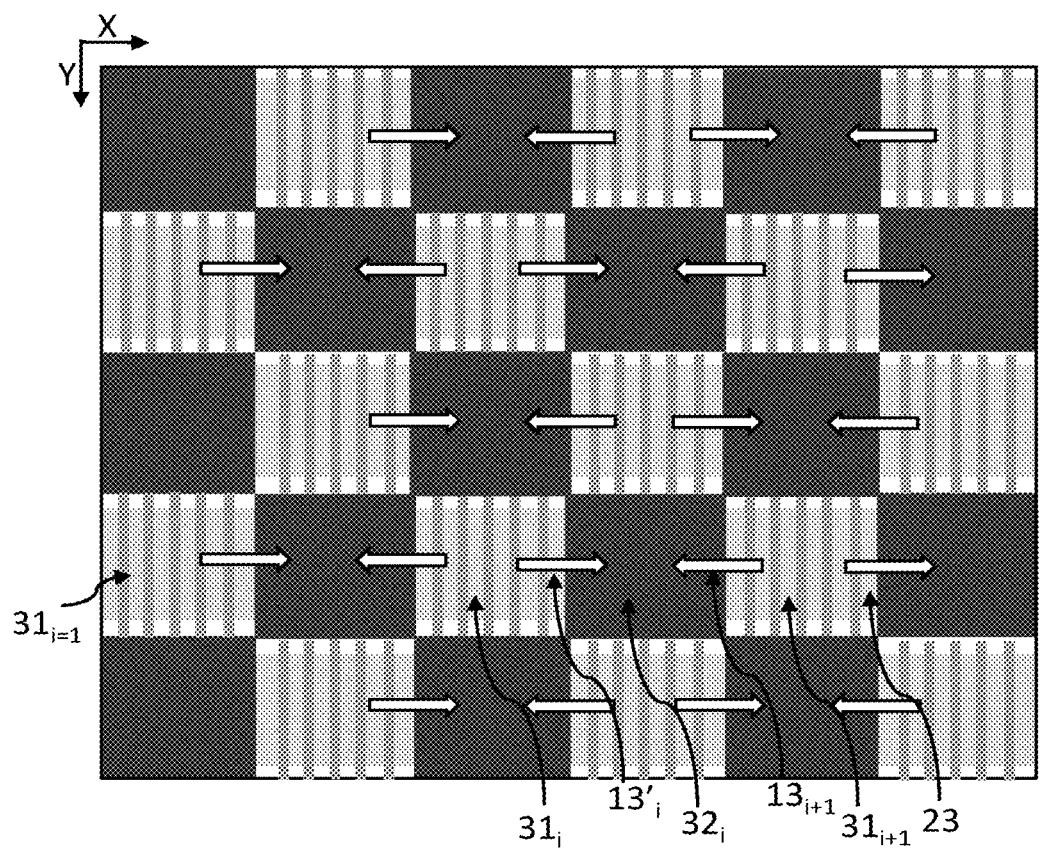
FIG. 1C shows a view of an image sensor shown schematically in FIG. 1A.

FIG. 1C shows a top view of an image sensor as shown in FIG. 1A. The position of the elementary masks $25_i$ and the openings $26_i$ in the form of a checkerboard can be seen. A masked pixel $32_i$ is positioned under each elementary mask $25_i$. A open pixel $31_i$ is positioned under each opening. With the exception of the pixels positioned on the periphery of the matrix, most of the masked pixels $32_i$ are positioned between two open pixels $31_{i-1}$, $31_i$, called adjacent open pixels, on the same row.

FIG. 1A shows pixels belonging to the same row, extending along a longitudinal axis X. A longitudinal waveguide 23 extends parallel to each row of pixels along the longitudinal axis X. Along a lateral axis Y, perpendicular to the longitudinal axis X, the longitudinal waveguide 23 has a width smaller than or equal to the width of the pixels. The axes X and Y are coplanar with the detection plane P. The waveguide 23 is preferably centered relative to the row of pixels facing which it extends. The waveguide forms a strip extending facing a plurality of pixels of the same row, while having a width smaller than or equal to the width of the pixels forming the row. Thus it takes the form of a strip extending parallel to the detection plane P. The refractive index of the material forming the waveguide 23 is greater than the refractive index of the materials to which it is adjacent.

A first diffraction grating $21_i$ is arranged between each open pixel $31_i$ of the row of pixels and the opening $26_i$ associated with said pixel. "Diffraction grating" is taken to mean a structure whose refractive index varies periodically at the scale of the wavelength $\lambda$, in one or more directions. The first diffraction grating is arranged $21_i$ in a thin layer, called the first thin layer, formed from a first material 21a, in which inclusions of a first auxiliary material 21b are positioned in a periodic manner. The first auxiliary material 21b is different from the first material 21a. Preferably, the first material 21a and the first auxiliary material 21b are dielectric materials, transparent in some or all of the spectral band $\Delta\lambda$ of the incident light wave $12_i$ propagating through the opening $26_i$. The respective refractive indices of the first material 21a and the first auxiliary material 21b are different. In the example described, the first material 21a forming the thin layer is silicon dioxide ($SiO_2$), while the first auxiliary material 21b forming the inclusions is silicon nitride (SiN). In this example, the first thin layer has a thickness of 50 nm along the axis Z.

The inclusions visible in FIGS. 1A, 1B and 1C, define a periodic spatial pattern with a period $P_1x$ of 240 nm. The first diffraction grating $21_i$ is a one-dimensional diffraction grating, in the sense that its periodicity is defined in a single dimension, in this case along the axis X. FIGS. 1A and 1B show a first diffraction grating $21_{i-1}$, $21_i$, $21_{i+1}$ associated, respectively, with the open pixels $31_{i-1}$, $31_i$ and $31_{i+1}$.

The inclusions of the first auxiliary material 21b here have a small length along the longitudinal axis X, of the order of 80 to 160 nm, and extend over some or all of the width of the pixel along the lateral axis Y, for example over 80% to 100% of this width.

The diffraction grating $21_i$ acts as a coupling grating for coupling part of the incident light wave $12_i$, propagating toward the open pixel $31_i$ along the axis Z, into the longitudinal waveguide 23. Such a coupling is known, and has been described, for example, in EP3147646, or in publications, for example the publication by D. Taillaert, "Compact efficient broadband grating coupler for silicon-on-insulator waveguides", Optics Letters, Vol. 29, N° 23, Dec. 1, 2004. The material forming the longitudinal waveguide 23 is, in this example, silicon nitride. It then corresponds to the first auxiliary material 21b of the first diffraction grating. It may be another material, provided that its refractive index is greater than the refractive index of the first material 21a and than the refractive index of the material of a lower layer 27, the latter extending between the matrix of pixels and the waveguide 23. The thickness of the waveguide 23 along the axis Z is 100 nm.

In this example, the material forming the lower layer 27 is silicon dioxide ($SiO_2$). The thickness of the lower layer 27 along the axis Z is 170 nm.

As a general rule, the period $P_1x$ of the pattern forming the first diffraction grating corresponds to the resonance wavelength $\lambda$ of the first diffraction grating divided by an actual optical index $n_{eff}$, so that $$P_{1,X} = \frac{\lambda}{n_{eff}}$$

$n_{eff}$ is between the refractive index of the first material $21a$, in this case silicon ($SiO_2$), and the refractive index of the material forming the waveguide 23.

When the incident wave $12_i$ propagates, through an opening $26_i$, toward an open pixel $31_i$, facing the opening, part of the incident wave $12_i$ is coupled, by the first diffraction grating $21_i$, into the waveguide 23. It then forms a confined wave propagating in the waveguide. The first diffraction grating $21_i$ then forms an injection grating, because it injects part of the incident light wave $12_i$ into the waveguide 23. Because of the angle of incidence of the incident light wave $12i$, which is orthogonal or substantially orthogonal to the plane along which the first diffraction grating $21_i$ extends, the coupling in the first diffraction grating creates:
- a confined wave $13_i$ propagating in a direction of propagation, in the waveguide 23, toward a masked pixel $32_{i-1}$;
- a confined wave $13'_i$, propagating in the opposite direction to the confined wave $13_i$, toward a masked pixel $32_i$.

Thus approximately 50% of the incident wave coupled into the waveguide 23 propagates in one direction, while 50% of the coupled incident wave propagates in an opposite direction in the waveguide. Along the two directions of propagation, the confined waves $13_i$ and $13'_i$ have the same amplitude and the same phase.

The part of the incident light wave $12'_i$ that is not coupled by the first diffraction grating $21_i$ is transmitted by the latter and propagates toward the open pixel $31_i$, where its intensity may be measured. Thus each open pixel $31_i$ forms an "intensity" pixel, because it can measure an intensity of the incident light wave $12_i$. It is considered that 25% of the incident wave $12_i$ may be coupled into the waveguide 23, this percentage possibly being smaller.

FIG. 1A also shows coupled waves $13_{i+1}$ and $13'_{i+1}$, resulting from the coupling of the incident wave $12_{i+1}$ to the first diffraction grating $21_{i+1}$, and propagating, respectively, in the waveguide 23 toward the masked pixels $32_i$ and $32_{i+1}$. Also shown is a coupled wave $13'_{i-1}$ resulting from the coupling of the incident wave $12_{i-1}$ to the first diffraction grating $21_{i-1}$, and propagating, respectively, in the waveguide 23 toward the masked pixel $32_{i-1}$. Also shown are the light waves $12'_{i-1}$ and $12'_{i+1}$ which are transmitted, respectively, by the first diffraction gratings $21_{i-1}$ and $21_{i+1}$ toward the open pixels $31_{i-1}$ and $31_{i+1}$.

The image sensor 20 comprises a second diffraction grating $22_i$ extending at the level of each masked pixel $32_i$. The second diffraction grating $22_i$ is arranged in a thin layer, called the second thin layer, formed from a second material $22a$, in which inclusions of a second auxiliary material $22b$, different from the first material $22a$, are positioned. In this example, the second thin layer is formed from the same material as the first thin layer forming the first diffraction grating, namely $SiO_2$. Thus, the second material $22a$ is $SiO_2$. The auxiliary second material $22b$ may be a dielectric material such as SiN, but the inventors considered it preferable for the second auxiliary material $22b$ to be a metal, for example aluminum. By using a metal, it is possible to increase the decoupling ratio, that is to say the percentage of the light wave extracted from the waveguide. One advantage of aluminum is that it is compatible with most CMOS manufacturing methods. The function of the second diffraction grating $22i$ is to extract the light propagating in the waveguide 23. Thus,
- the first diffraction grating $21_i$, associated with each open pixel $31_i$, is an injection grating, designed to inject part of the incident light wave $12_i$ into the waveguide 23;
- the second diffraction grating $22_i$, associated with each masked pixel $32_i$, is an extraction grating, designed to extract a confined light wave propagating in the waveguide 23.

Preferably, coupling ratio of the first diffraction grating $21i$, that is to say the percentage of light wave $12_i$ coupled into the waveguide 23, is smaller than the decoupling ratio of the second diffraction grating $22i$.

As described above in relation to the first diffraction grating $21i$, the inclusions forming the second diffraction grating are periodic, and extend along the lateral axis Y, over some or all of the width of the pixel, for example between 80% and 100% of the width of the pixel. Their thickness along the Z axis is 50 nm. In this example, the inclusions are formed from aluminum, with a periodic interval $P_2x$ of 240 nm. The length of each inclusion, along the X axis, is between 80 and 160 nm. By the action of the second diffraction grating $22_i$, each confined light wave propagating in the waveguide 23 is decoupled, and forms a decoupled wave $14_i$ propagating toward the masked pixel $32_i$. FIG. 1A shows second diffraction gratings $22_{i-1}$ and $22_{i+1}$ associated with the masked pixels $32_{i-1}$ and $32_{i+1}$ respectively, as well as the decoupled light waves $14_{i-1}$ and $14_{i+1}$.

Advantageously, each elementary mask $25_i$ comprises a reflective face oriented toward the waveguide 23. Thus part of the decoupled wave propagates toward the mask and is then reflected to propagate toward the masked pixel $32_i$. This makes it possible to increase the intensity of the signal detected by the masked pixel $32_i$.

The design of the first and second diffraction gratings, and the determination of their resonance wavelength, may be carried out by means of computer code. This is because the properties of light propagation in diffraction gratings are dependent on their specific periodic arrangement, and may be modeled, by those skilled in the art, on the basis of Maxwell's space and time equations. In the present case, the diffraction gratings have been modeled using Rsoft software, implementing a finite difference time domain (FDTD) method. Preferably, the first and second diffraction gratings have the same resonance wavelength. In this example, the resonance wavelength $\lambda$ is 405 nm.

The sensor 20 comprises an upper layer 28, interleaved between the first or the second diffraction grating and the openings or the elementary masks. In this example, the upper layer 28 is formed from $SiO_2$, with a thickness of 150 nm.

A non-reflecting layer $24_i$ may be placed on each pixel, and notably on each masked pixel $32_i$. This may, for example, be a layer of SiN, with a thickness of 50 nm, that is to say the thickness of a quarter wave, equal to $$\frac{\lambda}{4n_{SiN}},$$

where $n_{SiN}$ denotes the refractive index of SiN. Such a layer is optional. FIG. 1A also shows non-reflecting layers $24_{i-1}$ and $24_{i+1}$ associated with the masked pixels $32_{i-1}$ and $32_{i+1}$ respectively.

FIG. 1B shows a variant of FIG. 1A, in which the second diffraction gratings $22_{i-1}$, $22_i$, $22_{i+1}$ are positioned along a thin layer extending between the waveguide 23 and the pixels. According to this embodiment, the first waveguides and the second waveguides are positioned along two opposite sides of the waveguide 23.

Let $I_i$ and $\varphi_i$ be the intensity and the phase of the light wave $12_i$. Let $I_{i+1}$ and $\varphi_{i+1}$ be the intensity and the phase of the light wave $12_{i+1}$. Let $2\tau$ be the coupling ratio of each first diffraction grating. At the first diffraction grating $21_i$, a confined light wave $13_i$ is formed according to a coupling ratio $\tau$, and the same applies to the confined light wave $13'_i$. Thus the light wave $12'_i$ propagating to the open pixel $31_i$ has an amplitude $A_i$ such that $$A_i = (1-2\tau)a_i e^{j\varphi_i} \quad (1)$$

where j denotes the imaginary unit of the complex number ($j^2 = -1$) and $a_i$ is the amplitude of the incident light wave $12_i$.

The luminous intensity detected by the open pixel $31_i$ is $$I_i = (1-2\tau)^2 a_i^2 \quad (1')$$

The same reasoning applies to the open pixel $31_{i+1}$. Thus the light wave $12'i+1$ propagating to the open pixel $31_{i+1}$ has an amplitude $A_{i+1}$ such that $$A_{i+1} = (1-2\tau)a_{i+1} e^{j\varphi_{i+1}} \quad (2)$$

where $a_{i+1}$ is the amplitude of the incident light wave $12_{i+1}$.

The luminous intensity detected by the open pixel $31_{i+1}$ is $$I_{i+1} = (1-2\tau)^2 a_{i+1}^2 \quad (2')$$

Part of the incident light wave $12_i$ is coupled by the first diffraction grating $21_i$ into the waveguide 23. It forms a guided light wave $13'_i$, propagating toward the second diffraction grating $22_i$, with an amplitude $$A^*_i = \tau a_i e^{j\varphi_i} \quad (3).$$

Similarly, part of the incident light wave $12_{i+1}$ is coupled by the first diffraction grating $21_{i+1}$ into the waveguide 23. It forms a guided light wave $13_{i+1}$, propagating toward the second diffraction grating $22_i$, with an amplitude $$A^*_{i+1} = \tau a_{i+1} e^{j\varphi_{i+1}} \quad (4).$$

As a result of the decoupling by the second diffraction grating $22_i$, a light wave $14_i$ is formed, having an amplitude $A'_i$, assuming total decoupling, and total reflection by the mask $25_i$, such that:

$$A'_i = A^*_i + A^*_{i+1} = \tau a_i e^{j\varphi_i} + \tau a_{i+1} e^{j\varphi_{i+1}} \quad (5)$$

The intensity $I'_i$ detected by the masked pixel $32_i$ is such that:

$$I'_i = |\tau a_i e^{j\varphi_i} + \tau a_{i+1} e^{j\varphi_{i+1}}|^2 \quad (6)$$

Therefore $I'_i = \tau^2 (a_i^2 + a_{i+1}^2 + 2a_i a_{i+1} \cos(\varphi_{i+1} - \varphi_i))$ (7).

The intensities $I_i$ and $I_{i+1}$, measured by the open pixels $31_i$ and $31_{i+1}$ respectively, may be used to estimate $a_i$ and $a_{i+1}$ respectively, according to the expressions (1') and (2').

When $a_i$ and $a_{i+1}$ are known, the intensity measured by the masked pixel $32_i$ may be used to estimate $\cos(\varphi_{i+1} - \varphi_i)$, from which it is possible to deduce $\varphi_{i+1} - \varphi_i$.

The coupling ratio $\tau$ is obtained either by construction or by experimental measurements, by illuminating the sensor 20 with a calibration light source whose intensity is controlled, without a sample 5 between the sensor 20 and the calibration light source. Let $a_c$ be the amplitude of the calibration light source; since the phase shift of the light wave between the two open pixels $31_i$ and $31_{i+1}$ is zero, we obtain, by applying expressions (1'), (2') and (7) respectively:

$$I_{i,c} = (1-2\tau)^2 a_c^2;$$

$$I_{i+1,c} = (1-2\tau)^2 a_c^2;$$

$$I'_{i,c} = 4\tau^2 a_c^2;$$

$I_{i,c}$, $I_{i+1,c}$ and $I'_{i,c}$ being the intensities measured by the open pixels $31_i$, $31_{i+1}$ and the masked pixel $32_i$ respectively during the calibration.

The ratio $$\frac{I'_{i,c}}{I_{i,c}}$$

may be used to determine $\tau$.

Expression (7) shows that the intensity measured by the masked pixel $32_i$ depends on the phase shift of the light waves $12_i$, $12_{i+1}$ illuminating the adjacent open pixels $31_i$ and $31_{i+1}$ respectively. In other words, the intensity measured by the masked pixel $32_i$ depends on a phase difference between the light waves $12_i$ and $12_{i+1}$. Thus the masked pixel $32_i$ may be used to access information relating to the phase shift between the incident light wave at the two open pixels $31_i$, $31_{i+1}$ which are adjacent to it. It is therefore called a "phase" pixel.

Figure 1D:
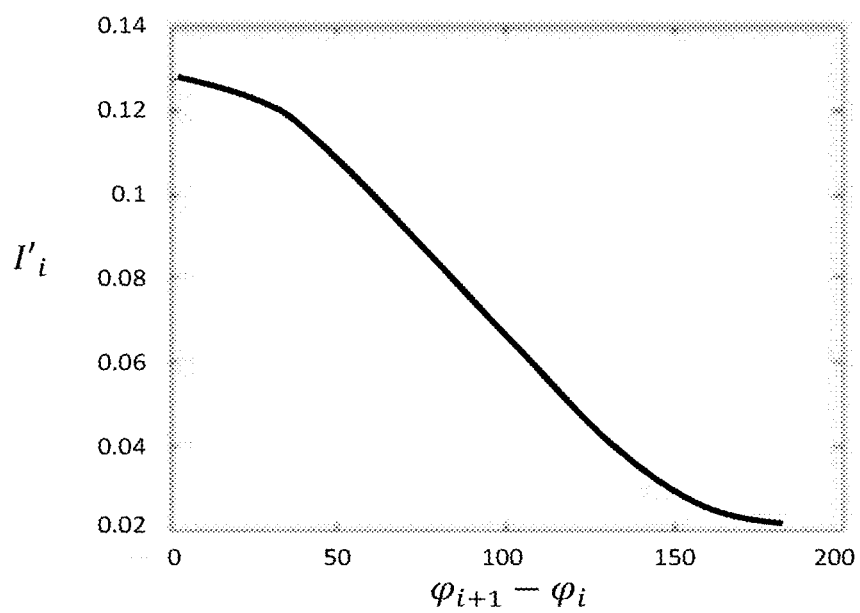
FIG. 1D shows a change in the intensity measured by a masked pixel as a function of a phase difference of a light wave propagating toward the open pixels adjacent to the masked pixel.

On the basis of simulations, the luminous intensity of a masked pixel was estimated as a function of the phase shift of the light waves incident on the open pixels adjacent to it. The result of the simulation is shown in FIG. 1D. The vertical axis represents the detected luminous intensity, while the horizontal axis represents the phase difference.

It will be seen that, when the waves $12_i$ and $12_{i+1}$ are in phase, the intensity measured by the masked pixel $32_i$ is maximal. When the waves $12_i$ and $12_{i+1}$ are in phase opposition, the intensity measured by the masked pixel $32_i$ is minimal.

The phase information obtained by each masked pixel $32_i$ is differential information, and represents a phase difference $\varphi_{i+1} - \varphi_i$ between the light waves $12_{i+1}$ and $12_i$ incident on the open pixels adjacent to the masked pixel. According to this embodiment, as may be seen in FIG. 1C, each masked pixel $32_i$ may be used to obtain a phase difference between the light waves incident on the open pixels which are adjacent to it along the same row. This is represented by the white arrows appearing in FIG. 1C, each white arrow representing the propagation of a guided wave between an open pixel and a masked pixel adjacent to it. If a known phase, called the reference phase $\varphi_{ref}$, is obtained on at least one pixel of each row, the phase $\varphi_i$ of each light wave incident on each open pixel $31_i$ in the same row may be progressively deduced. For example, if the phase $\varphi_1$ of the wave reaching the pixel $31_{i=1}$ located on the first column is known, the phase of the light waves incident on the other open pixels $31_i$ of the same row are deduced progressively, given the phase differences $\varphi_{i+1} - \varphi_i$ respectively measured by the masked pixels $32_i$ of the row.

Thus, as a general rule, the sensor 20 may be used to obtain, by means of each masked pixel $32_i$, a phase difference of the light waves $12_i$, $12_{i+1}$ incident, respectively, on the open pixels $31_i$, $31_{i+1}$ which are adjacent to it on the same row. By taking into account a reference phase $\varphi_{ref}$ on at least one pixel of the row, it is possible to obtain a phase value of the incident light waves reaching the open pixels of the same row. According to this embodiment, where the masked pixels of each row are independent from one row to another, it is preferably to take a reference phase $\varphi_{ref}$ into account on each row. "Independent masked pixels" is taken to mean that the masked pixels do not receive a guided light wave arriving from another row.

The reference phase $\varphi_{ref}$ may be determined by a conventional holographic reconstruction algorithm on the basis of the luminous intensity measured by an open pixel, this being done for each row. By comparison with the prior art, the holographic reconstruction may be limited to only one pixel per row, rather than all the pixels.

In the embodiment described with reference to FIG. 2A, a masked pixel $32_i$ as described above is shown. The masked pixel $32_i$ is adjacent in one row to two open pixels $31_i$ and $31_{i+1}$, similar to those described above. The masked pixel $32_i$ is also adjacent in one column to two open pixels $31_k$ and $31_{k+1}$. According to this embodiment:
- a longitudinal waveguide 23 extends facing the open pixels $31_i$, $31_{i+1}$ and facing the masked pixel $32i$. The longitudinal waveguide 23 extends along the longitudinal axis X. The dimension of the longitudinal waveguide 23 along the Y axis is less than or equal to the dimension of the pixels along this axis.
- a lateral waveguide 23' extends facing the open pixels $31_k$, $31_{k+1}$ and facing the masked pixel $32_i$. The lateral waveguide 23' extends along the lateral axis Y. The dimension of the lateral waveguide 23' along the X axis is less than or equal to the dimension of the pixels along this axis.

A first diffraction grating $21_i$, $21_{i+1}$, capable of coupling the incident light wave $12_i$, $12_{i+1}$ into the longitudinal waveguide 23, extends facing the open pixels $31_i$ and $31_{i+1}$. Thus, guided waves $13'_i$, $13_{i+1}$ propagate toward the masked pixel $32_i$, as described with reference to the first embodiment.

A first diffraction grating $21k$, $21_{k+1}$, capable of coupling the incident light wave $12_k$, $12_{i+1}$ into the lateral waveguide 23', extends facing the open pixels $31_k$ and $31_{k+1}$. Thus, guided waves $13'_k$, $13_{k+1}$ propagate toward the masked pixel $32_i$, in a similar way to what was described with reference to the first embodiment.

A second diffraction grating $22_i$, for decoupling both the wave propagating in the longitudinal waveguide 23 and the wave propagating in the lateral waveguide 23', extends facing the masked pixel $32_i$. The waves decoupled in this way propagate toward the masked pixel $32_i$.

In one configuration, the waveguides 23 and 23' are coplanar. They form a grid comprising strips that intersect facing each masked pixel $32_i$. The second diffraction grating $22_i$ is an identical two-dimensional grating, positioned at the intersection of the waveguides 23 and 23'. The periodicity of the two-dimensional grating is defined along the longitudinal axis X and the lateral axis Y. It enables the guided waves propagating along the two axes to be extracted toward the masked pixel $32_i$. Such two-dimensional gratings, in which the inclusions take the form of blocks arranged periodically along the X and Y axes, are described, for example, in EP3147646. Two-dimensional diffraction gratings are known to those skilled in the art.

In one configuration, notably when the waveguides 23 and 23' are not coplanar, the diffraction grating $22_i$ may consist of two one-dimensional diffraction gratings, as described with reference to the first embodiment. The diffraction grating $22_i$ then comprises

- a one-dimensional diffraction grating for extracting the guided waves $13'_i$ and $13_{i+1}$ propagating in the longitudinal waveguide 23;
- a one-dimensional diffraction grating for extracting the guided waves $13'_k$ and $13_{k+1}$ propagating in the lateral waveguide 23'.

By similar reasoning to that relating to the preceding embodiment:
the intensity detected by the pixel $31_i$ is $$I_i = (1-2\tau)^2 a_i^2; \quad (10)$$

the intensity detected by the pixel $31_{i+1}$ is $$I_{i+1} = (1-2\tau)^2 a_{+1}^2; \quad (11)$$

the intensity detected by the pixel $31_k$ is $$I_k = (1-2\tau)^2 a_k^2; \quad (12)$$

the intensity detected by the pixel $31_{k+1}$ is $$I_{k+1} = (1-2\tau)^2 a_{+1}^2 \quad (13)$$

the intensity detected by the pixel $32_i$ is $$I'_i = \tau^2(a_i^2 + a_{i+1}^2 + a_k^2 + a_{k+1}^2 + 2a_i a_{i+1} \cos(\varphi_{i+1}-\varphi_i) + 2a_k a_{k+1} \cos(\varphi_{k+1}-\varphi_k) + 2a_i a_k \cos(\varphi_i-\varphi_k) + 2a_i a_{k+1} \cos(\varphi_i-\varphi_{k+1}) + 2a_{i+1} a_k \cos(\varphi_{i+1}\varphi_k) + 2a_{i+1} a_{k+1} \cos(\varphi_{i+1}-\varphi_{k+1})) \quad (14)$$

Figure 2A:
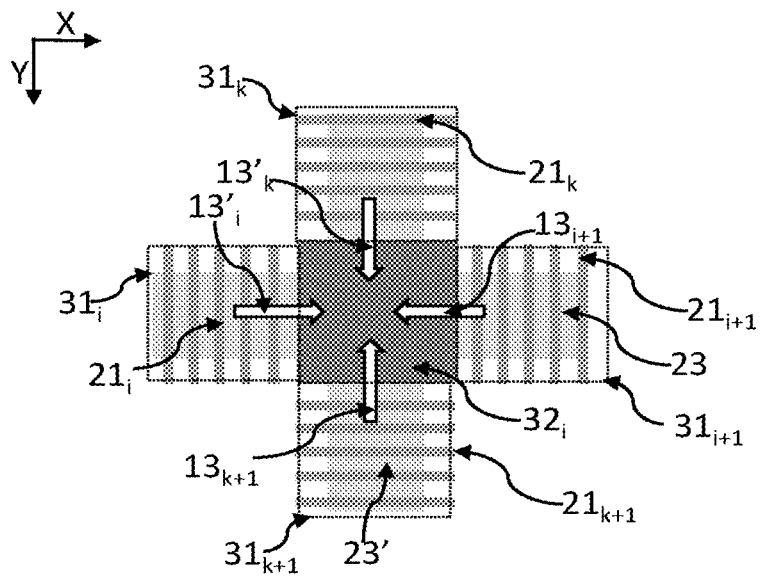
FIGS. 2A and 2B show another embodiment of an image sensor according to the invention.
Figure 2B:
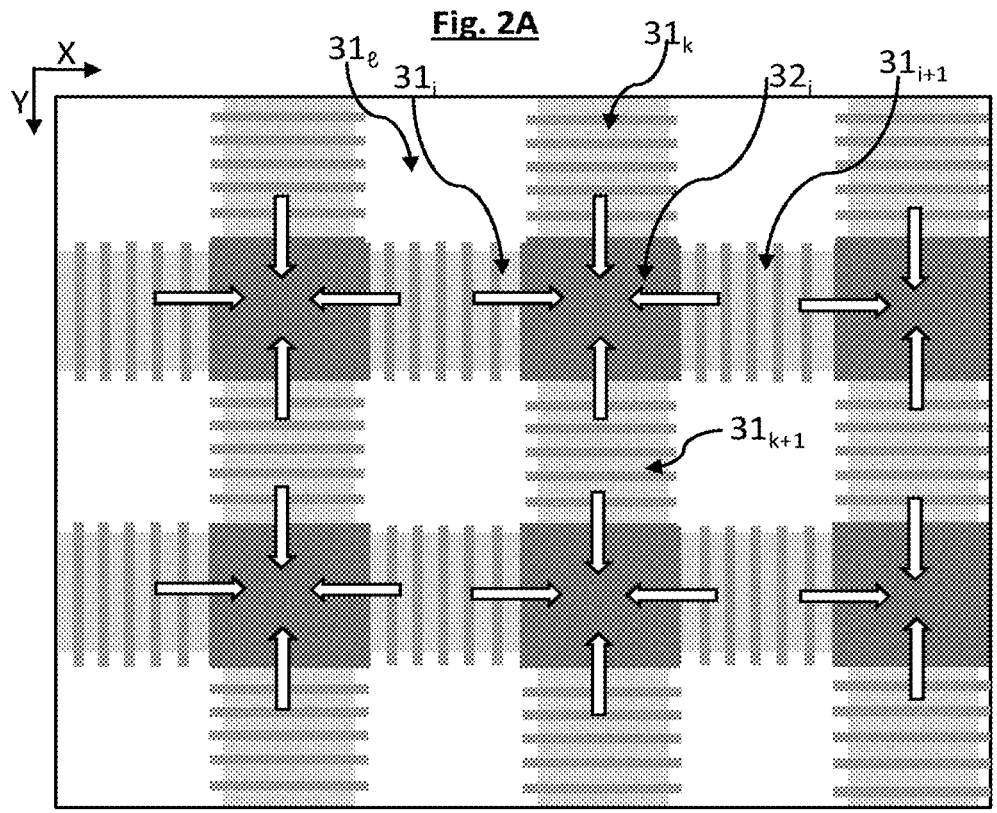

FIG. 2B is an illustration of an image sensor 20 whose pixels are arranged in the manner shown in FIG. 2A. It will be noted that the sensor 20 has three types of pixels:
- pixels $31_j$, not being associated with any diffraction grating, the latter being shown in white, and enabling the intensity $a_j^2$ of the light wave incident on them to be obtained.
- open pixels $31_i$, associated with a first coupling grating, whose measured intensity corresponds to one of the expressions (10) to (13).
- masked pixels $32_i$, such that information on the phase may be obtained, according to equation (14).

Such a sensor may be used to obtain good spatial resolution of the intensity, the number of pixels for obtaining information relating to the intensity being greater than the number of masked pixels. The phase information relating to the different masked pixels $32_i$ may be combined and form a system whose unknowns of which the phases $\varphi_i$ of the light waves $12_i$ incident on each open pixel $31_i$.

In FIG. 2B, each white arrow represents the propagation of a guided wave between an open pixel and a masked pixel adjacent to it, along the same row or the same column.

Figure 2C:
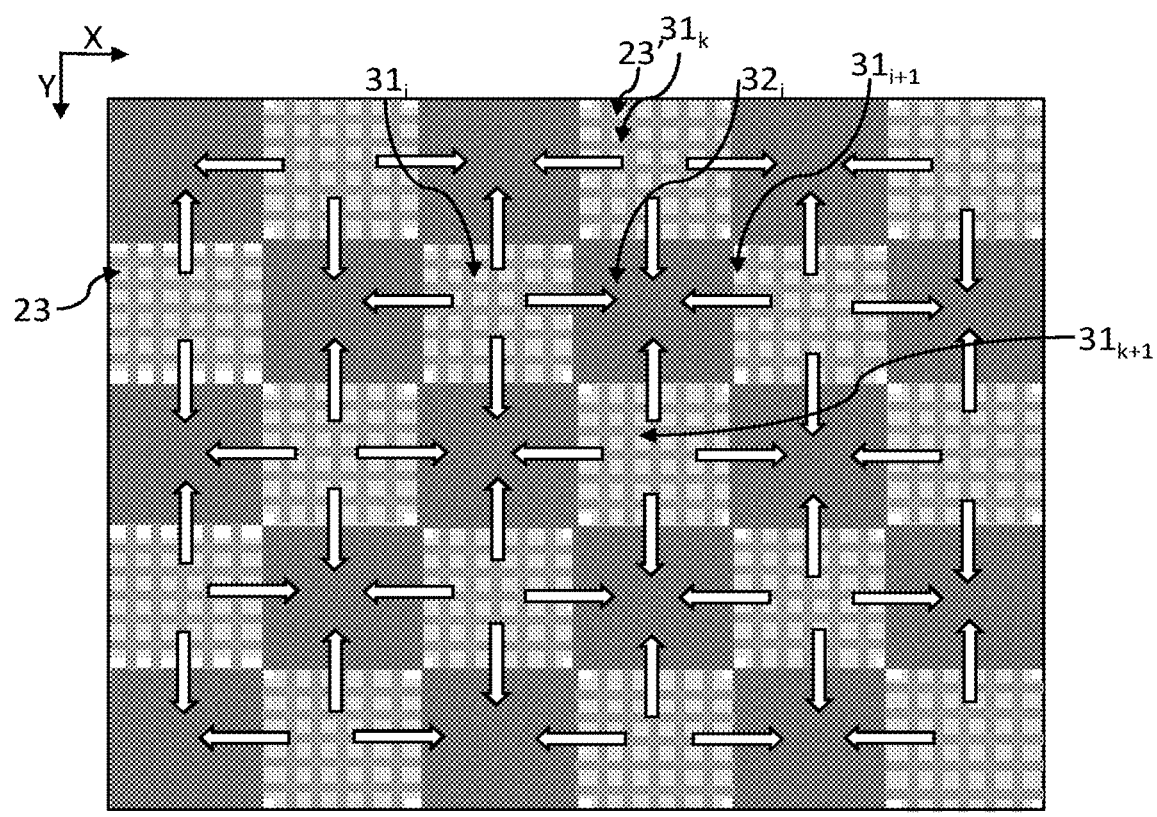
FIGS. 2C shows another embodiment of an image sensor according to the invention.

In another configuration, shown in FIG. 2C, the number of masked pixels $32_i$ is increased. By contrast with the configuration shown in FIGS. 2A and 2B, in such a configuration each first diffraction grating $21_i$ is a two-dimensional grating, for coupling the incident light wave $12_i$ into a longitudinal waveguide 23 and into a lateral waveguide 23'. In the same way as in the preceding configuration, the waveguides 23 and 23' extend along strips which are parallel to the longitudinal axis X and the lateral axis Y respectively. The dimension of each waveguide perpendicular to the axis along which it extends is less than or equal to the dimension of the pixels. Two waveguides, longitudinal and lateral respectively, intersect facing each open pixel $31_i$ and facing each masked pixel $32_i$. A two-dimensional diffraction grating $21_i$, for coupling part of the incident light wave $12_i$ into a longitudinal waveguide 23 and into a lateral waveguide 23', corresponds to each open pixel $31_i$. A two-dimensional diffraction grating $22_i$, for extracting guided waves propagating in the waveguides 23, 23' and converging toward the two-dimensional diffraction grating $22_i$, corresponds to each closed pixel $32_i$. This results in the formation of a decoupled light wave $14_i$ propagating toward the masked pixel $32_i$. The structure of the two-dimensional waveguides corresponds to that described with reference to the second waveguide $22_i$ shown in FIG. 2A. The luminous intensities detected at the pixels $31_i$, $31_{i+1}$, $31_k$, $31_{k+1}$ and $32_i$, shown in FIG. 2C, correspond to the expressions (10) to (14) explained in the preceding embodiment. Such an embodiment may be used to increase the number of masked pixels, making it possible to improve the spatial resolution relating to the phase information.

In FIG. 2C, each white arrow represents the propagation of a guided wave between an open pixel and a masked pixel adjacent to it, along the same row or the same column.

FIGS. 3A to 3L show the main steps of a method of manufacturing a sensor 20 as described in the preceding embodiments.

Figure 3A:
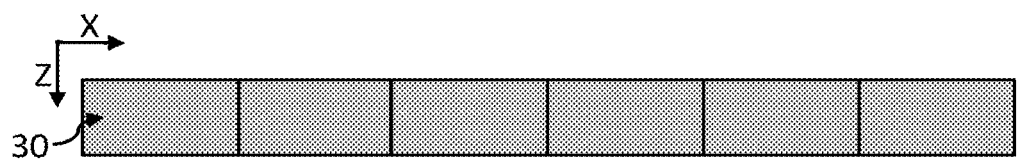
FIGS. 3A to 3L show steps in the manufacture of an image sensor as shown in FIG. 1A.

FIG. 3A: the method starts with a substrate comprising a matrix 30 of CMOS photodiodes forming pixels.

Figure 3B:

FIG. 3B: a layer 24 of SiN is deposited for the purpose of forming the non-reflective layer 24, described above. This step is optional.

Figure 3C:
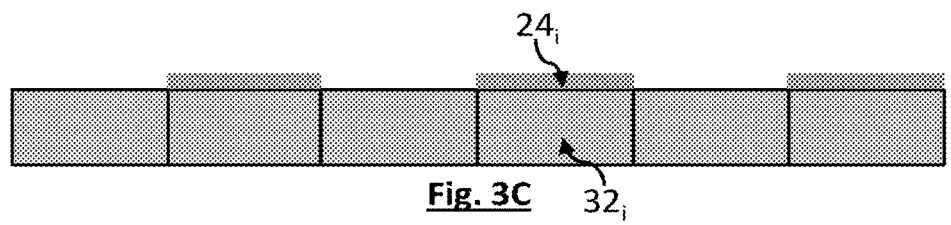

FIG. 3C: the SiN layer 24 is etched to provide a non-reflective block $24_i$ at the position of each masked pixel $32_i$. This step, like the preceding one, is optional.

Figure 3D:
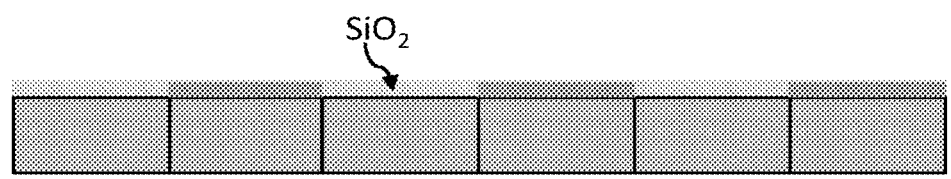

FIG. 3D: deposition of a layer of S102 between each non-reflective block $24_i$, and chemical-mechanical polishing (CMP).

Figure 3E:
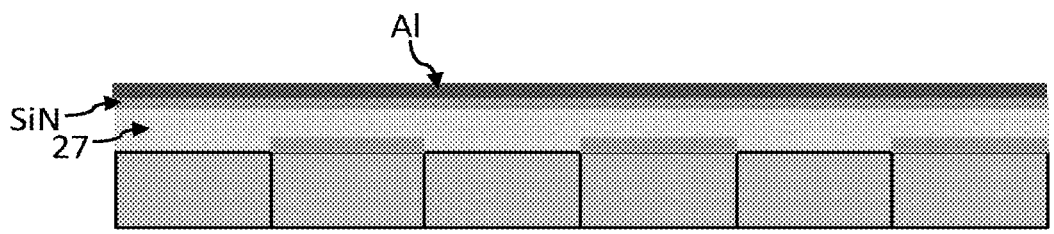

FIG. 3E: deposition of a layer of $SiO_2$ forming the lower layer 27, then deposition of the layer of SiN, forming the waveguide 23, then deposition of a layer of Al, forming the second auxiliary material 22b of the second diffraction grating $22_i$.

Figure 3F:
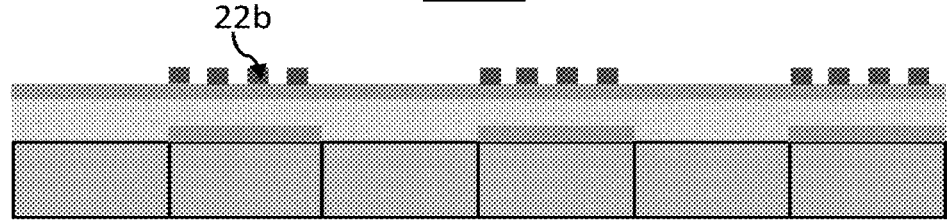

FIG. 3F: etching of the layer of Al, so as to form the second diffraction grating $22_i$ facing each masked pixel $32_i$.

Figure 3G:
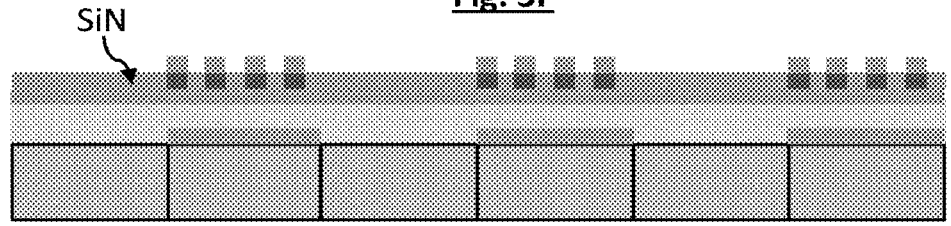

FIG. 3G: conforming deposition of a layer of SiN, forming the first auxiliary material 21b of the first diffraction grating $21_i$.

Figure 3H:
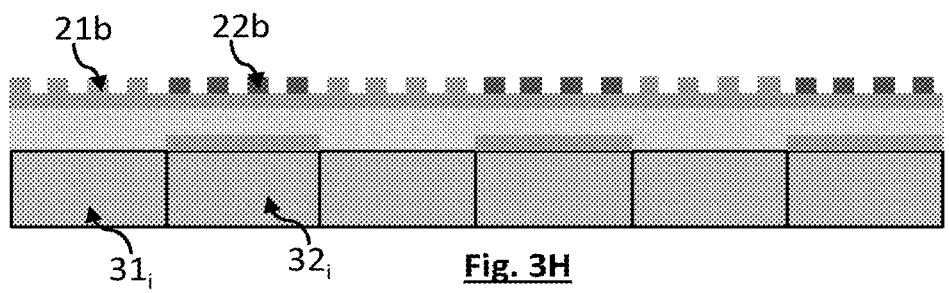
Figure 3I:
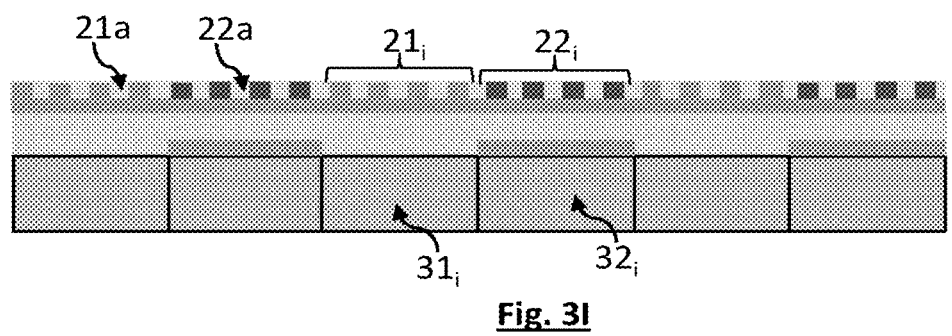

FIG. 3H: etching of the SiN;

FIG. 3I: deposition of $SiO_2$, forming the first material 21a of the first diffraction grating $21_i$ and the second material 22b of the second diffraction grating $22_i$, and chemical mechanical polishing.

Figure 3J:
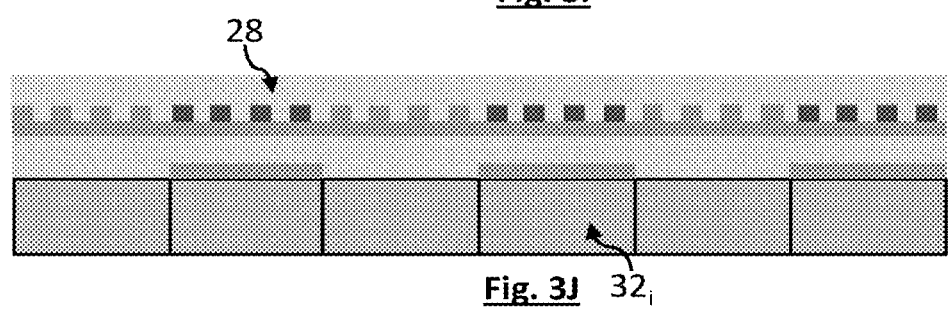

FIG. 3J: deposition of $SiO_2$ to form the upper layer 28.

Figure 3K:
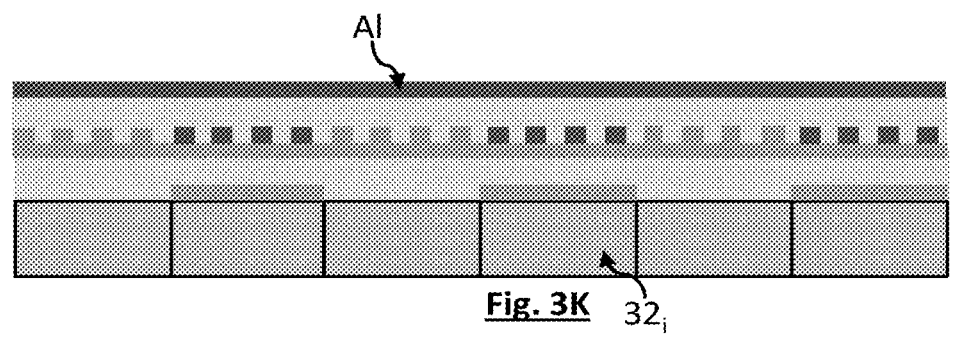

FIG. 3K: deposition of a layer of aluminum to form the mask 25.

Figure 3L:
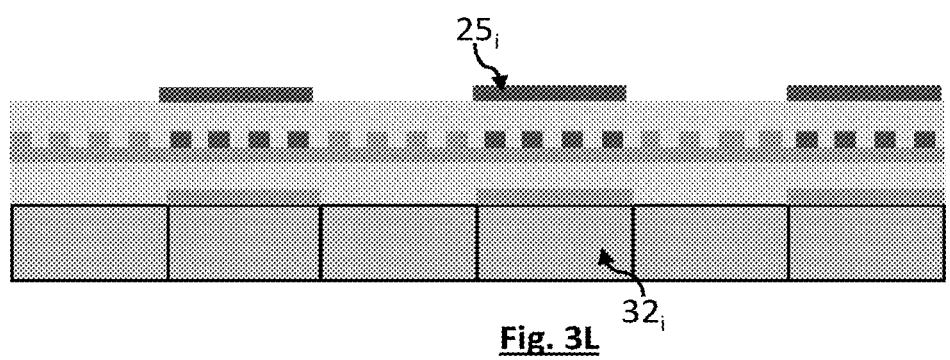

FIG. 3L: etching of the layer of aluminum, so as to form blocks $25_i$, each block corresponding to an elementary mask $25_i$ extending facing a masked pixel $32_i$.

FIGS. 4A to 4J show simulations of images corresponding to the observation of a sample using the device shown in FIG. 1A. The sample is modeled by a set of 10 μm diameter disks having constant absorption and random phase, distributed over a plane. FIGS. 4A and 4B show the spatial distribution of the absorption and the phase, respectively. The modulus and the phase of a hologram formed on the detection plane P was simulated, as shown in FIGS. 4C and 4D respectively. FIG. 4C corresponds to an image obtained by the open pixels (intensity pixels). FIG. 4E shows a phase difference between two neighboring open pixels on the same row.

On the basis of the modulus of the hologram (FIG. 4C), a holographic reconstruction algorithm, as described in patent application WO2017162985, was applied. This may be used to obtain a spatial distribution of the modulus and the phase of the light wave incident on the image sensor, in the plane of the sample. The distribution of the modulus and the phase correspond to FIGS. 4F and 4G respectively.

The image of FIG. 4G may be used to obtain an estimate of the phase of the light wave, at the position of at least one pixel per row of the image sensor 20, this estimate forming a reference phase. For this purpose, it is simply necessary to propagate the image of FIG. 4G in the detection plane, in certain pixels, so as to obtain the reference phase. When at least one reference phase per row is known, and on the basis of the differential phase measurements shown in FIG. 4E, a distribution of the phase is obtained at the position of each open pixel of the image sensor. This is shown in FIG. 4H.

On the basis of the distribution of the modulus of the incident light wave, in the detection plane, measured by the sensor (FIG. 4C), and the distribution of the phase obtained in FIG. 4H, phase and modulus information at the detection plane becomes available. By applying a simple holographic propagation algorithm, it is possible to reconstruct an image of the modulus (FIG. 4I) and an image of the phase (FIG. 4J) of the light wave in the plane of the sample. This then provides a usable representation of the sample.

Thus a key point of the invention is that a luminous intensity representative of the phase of the light wave incident on the sensor is obtained by means of masked pixels of the image sensor. More precisely, the measured luminous intensity corresponds to a phase difference between pixels adjacent to each masked pixel. On the basis of a reference phase, or by solving a system of equations, the invention makes it possible to estimate a spatial distribution of the phase of the light wave at the pixels of the sensor, while also enabling a spatial distribution of the intensity of the light wave at the pixels of the sensor to be obtained. The information relating to the phase and intensity obtained in the detection plane may be used to propagate the light wave in space, and notably in the plane of the sample, so as to permit an analysis of the latter.

Therefore the sensor according to the invention may be used in the observation of samples, particularly transparent or translucent samples. The invention may be used in the field of biology, for example in the observation of cells or microorganisms, or in the field of diagnostic medicine, by permitting precise observation of samples. It may also be used in monitoring industrial processes or in environmental monitoring, when transparent or translucent samples are analyzed.

The invention claimed is:

1. An image sensor comprising a matrix of pixels, extending along a detection plane, and configured to form an image of an incident light wave propagating, in a spectral band, along a propagation axis, the image sensor comprising a mask, formed by opaque elementary masks, extending parallel to the detection plane, between which there extend openings through which the incident light wave can propagate toward the detection plane, the matrix of pixels being divided into:

open pixels extending facing the openings;

masked pixels, each masked pixel being defined by a projection of an elementary mask along the axis of propagation on the matrix of pixels, each masked pixel being associated with the elementary mask facing it;

the image sensor comprising, between the open pixels and the openings:

a waveguide, forming a strip extending facing masked pixels and open pixels;

a first diffraction grating, extending facing at least one open pixel, and configured to couple part of the incident light wave into the waveguide, so as to form a guided wave;
the first diffraction grating being configured to transmit another part of the incident light wave toward the open pixel;
the first diffraction grating being associated with the open pixel;
a second diffraction grating, extending facing a masked pixel, and configured to extract part of the guided wave propagating in the waveguide, so as to form an extracted wave, so that the extracted wave propagates toward the masked pixel; the second diffraction grating being associated with the masked pixel.

2. The image sensor as claimed in claim 1, wherein:
a masked pixel extends between two open pixels which are adjacent to it, each open pixel being associated with a first diffraction grating;
the waveguide extends facing two open pixels and facing the masked pixel;
the masked pixel is associated with a second diffraction grating, so as to extract light waves guided in the waveguide, resulting, respectively, from a coupling of the incident light wave by the first diffraction grating associated with each open pixel adjacent to the masked pixel.

3. The image sensor as claimed in claim 2, wherein the masked pixel and the open pixels adjacent to it are arranged along a same row or along a same column of the matrix of pixels.

4. The image sensor as claimed in claim 1, wherein:
a masked pixel extends between two open pixels, which are adjacent to it, along a row of the matrix of pixels, each open pixel being associated with a first diffraction grating;
the waveguide extends facing the two open pixels and facing the masked pixel, parallel to the row, forming a longitudinal waveguide, each first diffraction grating associated with the open pixels of the row being configured to couple part of the incident light wave into the longitudinal waveguide, thereby forming guided light waves propagating into the longitudinal waveguide;
the masked pixel is associated with a second diffraction grating, the second diffraction grating being configured to extract part of the guided light waves propagating into the longitudinal waveguide, thereby forming a light wave extracted from the longitudinal waveguide, so that part of the light wave extracted from the longitudinal waveguide is detected by the masked pixel;
the masked pixel extends between two open pixels, which are adjacent to it, along a column of the matrix of pixels, said open pixels of the column being associated with a first diffraction grating;
the sensor comprises a lateral waveguide extending parallel to the column, facing the two open pixels of the column and facing the masked pixel, each first diffraction grating associated with the open pixels of the column being configured to couple part of the incident light wave into the lateral waveguide, thereby forming guided light waves propagating into the lateral waveguide;
the second diffraction grating is configured extract part of the guided light waves propagating into the lateral waveguide, thereby forming a light wave extracted from the lateral waveguide, so that part of the light wave extracted from the lateral waveguide is detected by the masked pixel.

5. The image sensor as claimed in claim 1, wherein
the first diffraction grating is formed by a first thin layer, extending parallel to the waveguide, the first thin layer being formed from a first material, the first thin layer comprising inclusions of a first auxiliary material, the respective refractive indices of the first material and of the first auxiliary material being different, the first material and the first auxiliary material being transparent in part or all of the spectral band;
the second diffraction grating is formed by a second thin layer, extending parallel to the waveguide, the second thin layer being formed from a second material, the second thin layer comprising inclusions of a second auxiliary material, the respective refractive indices of the second material and of the second auxiliary material being different.

6. The image sensor as claimed in claim 5, wherein the first material and the second material are the same material.

7. The image sensor as claimed in claim 5, wherein the second auxiliary material is a metal.

8. The image sensor as claimed in claim 1, wherein the first diffraction grating and the second diffraction grating extend along the same plane.

9. The image sensor as claimed in claim 1, wherein the first diffraction grating and the second diffraction grating extend parallel to the matrix of pixels.

10. The image sensor as claimed in claim 1, in which at least one elementary mask comprises a reflective face, facing a masked pixel associated with the elementary mask, so as to reflect part of the light wave extracted from the waveguide, extending facing the masked pixel, toward the latter.

11. A device for observing a sample, comprising:
a light source configured to emit an illuminating light wave in a spectral band, the illuminating light wave propagating along a propagation axis, toward the sample;
an image sensor;
a holder configured to receive the sample, so that the sample extends between the light source and the sample, the image sensor being configured to detect an incident light wave propagating between the sample and the sensor when the sample is illuminated by the illuminating light wave;
the image sensor being a sensor as claimed in claim 1.

12. A method for determining an intensity and a phase of a light wave, using an image sensor as claimed in claim 1, the image sensor being such that:
a masked pixel extends along a row or a column between two open pixels;
the waveguide extends facing the open pixels and facing the masked pixel, along the row or along the column;
each of the open pixels is associated with a first diffraction grating;
the masked pixel is associated with a second diffraction grating;
the method comprising:
a) illuminating the sensor in such a way that an incident light wave propagates toward each open pixel;
b) coupling part of the incident light wave, by means of the first diffraction grating extending facing each open pixel, in such a way that:
at the first diffraction grating, a confined light wave propagating in the waveguide is formed;

a transmitted light wave is transmitted to the open pixel associated with the first diffraction grating;

c) extracting, by means of the second diffraction grating, part of each confined light wave propagating in the waveguide, so as to form an extracted light wave;

d) detecting part of the extracted light wave by the masked pixel;

e) obtaining, on the basis of an intensity of the extracted light wave, information relating to the phase difference of the incident light wave propagating toward each open pixel, respectively;

f) detecting the light wave transmitted by the first diffraction grating toward each open pixel associated with the first diffraction grating, in order to obtain an intensity of the transmitted light wave representative of the intensity of the light wave incident on each open pixel.

13. The method as claimed in claim 12, comprising:

g) estimating a phase of the light wave detected by each open pixel on the basis of the phase difference obtained in e).

14. The method as claimed in claim 13, wherein the open pixels are positioned along the same row or the same column of the matrix of pixels, and wherein g) comprises taking into account a reference phase value, obtained on a pixel of the row or of the column.

15. The method as claimed in claim 13, wherein the sensor comprises masked pixels, each masked pixel being positioned between at least two open pixels along the same row and two open pixels along the same column, and wherein a) to f) are carried out on each masked pixel as well as on the open pixels between which the masked pixel is positioned, and wherein g) is carried out on the basis of a phase difference determined on the basis of an intensity of a light wave detected by each masked pixel.

* * * * *